(12) United States Patent
Omori et al.

(10) Patent No.: US 8,419,705 B2
(45) Date of Patent: *Apr. 16, 2013

(54) APPARATUS FOR SEPARATING AND STORING BLOOD COMPONENTS

(75) Inventors: Masayoshi Omori, Hiroshima (JP); Seishin Tanaka, Hiroshima (JP); Yasunori Okamoto, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 586 days.

This patent is subject to a terminal disclaimer.

(21) Appl. No.: 12/670,971

(22) PCT Filed: Jul. 25, 2008

(86) PCT No.: PCT/JP2008/063366
§ 371 (c)(1),
(2), (4) Date: Jan. 27, 2010

(87) PCT Pub. No.: WO2009/017041
PCT Pub. Date: Feb. 5, 2009

(65) Prior Publication Data
US 2010/0211041 A1    Aug. 19, 2010

(30) Foreign Application Priority Data

Jul. 30, 2007  (JP) .................................. 2007-197787

(51) Int. Cl.
*A61B 19/00*    (2006.01)
(52) U.S. Cl.
USPC ........................................................ 604/403

(58) Field of Classification Search ................. 604/6.01, 604/6.04, 409, 405, 406, 408, 410, 319–321, 604/541, 543; 424/93.2; 220/501, 502
See application file for complete search history.

(56) References Cited

U.S. PATENT DOCUMENTS

| 4,447,220 A | 5/1984 | Eberle |
| 5,275,585 A * | 1/1994 | Olson ........................... 604/319 |
| 2006/0251622 A1* | 11/2006 | Suzuki et al. ................ 424/93.2 |

* cited by examiner

*Primary Examiner* — Philip R Wiest
(74) *Attorney, Agent, or Firm* — Muncy, Geissler, Olds & Lowe, PLLC

(57) ABSTRACT

It is intended to provide an apparatus for separating and storing blood components which facilitates the preparation of serum. An apparatus (1) for separating and storing blood components which comprises a blood pooling part (2) for pooling a fluid at least containing liquid components containing a blood-origin coagulation factors and platelets, a component storing part (3) for storing at least a part of the components of the fluid pooled in the blood pooling part (2), and a connector part (4) aseptically connecting the blood pooling part (2) to the component storing part (3), wherein the blood pooling part (2) comprises a blood pooling container (21) in the form of a flexible tube, a fluid inlet channel (27) for introducing the fluid into the blood pooling container (21) and a component outlet channel (28) for leading out at least a part of the components of the fluid; the component storing part (3) has a component inlet channel (37) for introducing at least a part of the components of the fluid having been led out from the blood pooling container (21); and the connector part (4) connects the component outlet channel (28) to the component inlet channel (37).

10 Claims, 10 Drawing Sheets

APPARATUS FOR SEPARATING AND STORING BLOOD COMPONENTS

TECHNICAL FIELD

The present invention relates to an apparatus for separating and storing blood components.

BACKGROUND ART

Currently, in the field of regenerative medicine, studies in which stem cells collected from a subject are caused to proliferate or differentiate ex vivo, and are thereafter transplanted into a subject, thereby promoting regeneration of tissue of the subject, have been carried out. Stem cells are multipotent and can differentiate into a variety of tissues and organs, and they have been attracting attention as cells which are the key to regenerative medicine.

It has been known that in ex vivo cultural proliferation of stem cells, the addition of a serum to the medium is effective. However, when human therapies are targeted, the use of a serum derived from an animal other than humans should be avoided in light of possible safety problems. Therefore, the use of a serum prepared from blood collected from a human, in particular, collected from the same subject is desired. Furthermore, in comparison to a blood test, cultivation of stem cells in the field of regenerative medicine requires a relatively large amount of serum. In addition, in order to prepare serum assuming application to a human, it is required to separate and store the serum aseptically in a closed system.

As a response to the abovementioned various requirements, the present applicants have already disclosed a serum preparation apparatus including: a blood storage part for storing blood, and a component storage part linked aseptically and in an air-tight manner to the blood storage part, the blood storage part having a blood coagulation accelerating substance that is in contact with the blood and accelerates coagulation, and the blood coagulation accelerating substance producing serum aseptically (refer to Patent Document 1).

Patent Document 1: Japanese Patent No. 3788479

DISCLOSURE OF THE INVENTION

Problems to be Solved by the Invention

The serum preparation apparatus described in Cited Reference 1 can produce serum quickly and efficiently while ensuring a high level of safety. In the serum preparation apparatus described in Patent Document 1, in order to separate blood stored in a blood storage part into blood clots including hemocyte components such as erythrocytes and the like, and serum, which is a humoral component, separation by a centrifuge separator is required. At this occasion, in order to prevent the serum from being contaminated by microbes and the like, it is necessary to apply the entire serum preparation apparatus, including the blood storage part and the component storage part linked aseptically thereto, to the centrifuge separator.

However, in the serum preparation apparatus described in Patent Document 1, the blood storage part and the component storage part are each configured from a flexible bag in which two sheets of polyvinyl chloride are layered on each other, and which is formed in a bag shape by welding peripheries thereof together. In order to apply the entire serum preparation apparatus that has a plurality of this type of bag to the centrifuge separator, it has been necessary to use a protective bag dedicated to controlling by holding a disposition of the plurality of bags. On this account, the entire serum preparation apparatus becomes large, a relatively big centrifuge separator is necessary, and it could be said that the apparatus does not have general versatility. Furthermore, since the blood storage part is formed from a bag that has flexibility, it is difficult to maintain the disposition of the blood storage part, and after separation of the blood components, disorder has easily occurred at an interface between the separated serum and settled blood components. In addition, since the blood storage part is formed from a bag possessing flexibility, it has been relatively difficult to confirm the quantity contained in the blood storage part. As a result there has been a demand for an apparatus for separating and storing blood components in which serum can be prepared more easily.

Consequently, it is an object of the present invention to provide an apparatus for separating and storing blood components in which serum can be prepared more easily.

Means for Solving the Problems

The present invention provides an apparatus for separating and storing blood components, the apparatus having: a blood storage part for storing fluid including at least a blood derived humoral component and platelets; a component storage part for storing at least a part of the components of the fluid stored in the blood storage part; and a linking part for aseptically linking the blood storage part and the component storage part; wherein the blood storage part has a blood storage container of cylindrical shape, which has flexibility, a fluid inlet channel for introducing the fluid into the blood storage container, and a component outlet channel for extracting at least a part of the components of the fluid from the blood storage container; the component storage part has a component inlet channel for introducing at least a part of the components of the fluid that have been extracted from the blood storage container; and the linking part links the component outlet channel and the component inlet channel; and thus the abovementioned object realized.

Effects of the Invention

According to the present invention it is possible to provide an apparatus for separating and storing blood components in which a serum can be prepared more easily.

Figure 1:
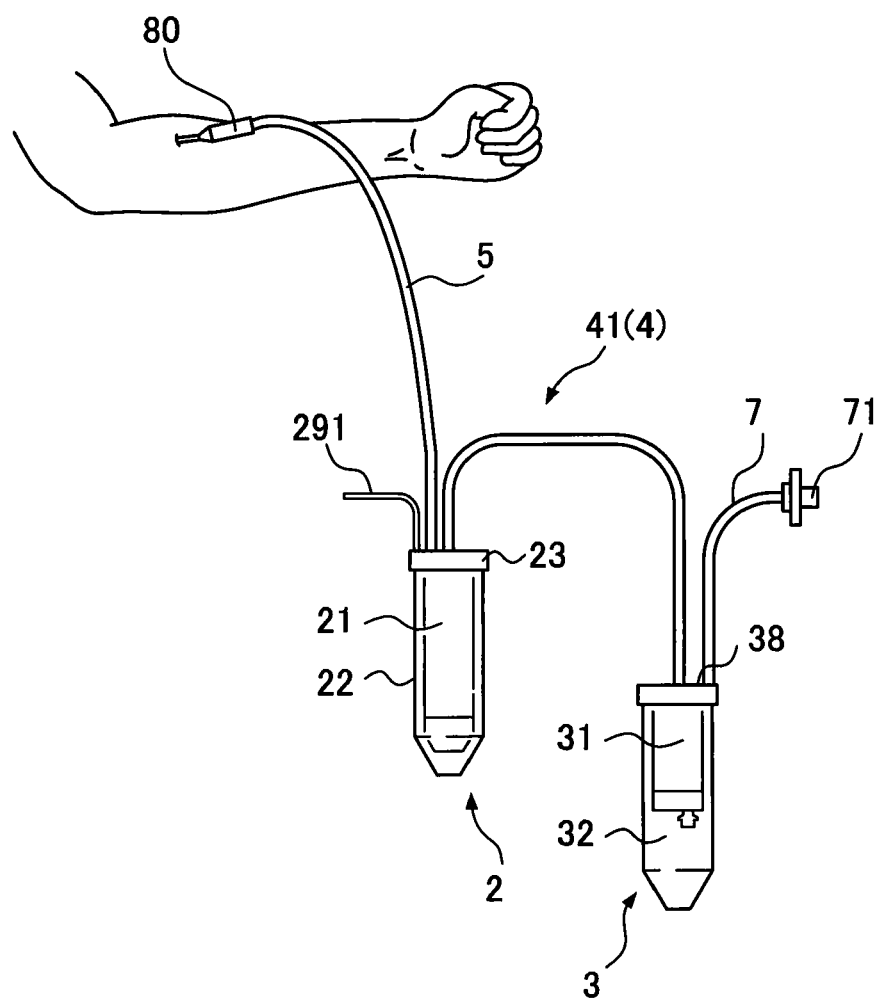
FIG. 1 is a drawing showing a first embodiment of the apparatus for separating and storing blood components of the present invention.

EXPLANATION OF REFERENCE NUMERALS 1 apparatus for separating and storing blood components
2 blood storage part
21 blood storage container
22 first storage container
23 first cap
24 first connecting part
25 second connecting part
26 pressure regulation space
27 fluid inlet channel
28 component outlet channel
29 injection hole
3 component storage part
31 component storage container
32 second storage container
33 second cap
34 component collection orifice
35 third connection part
36 fourth connection part
37 component inlet channel
38 ventilation channel
4 linking part
41 linking tube
5 blood drawing tube
6 blood coagulation accelerating substance
7 ventilation tube
71 ventilation filter
80 blood drawing needle Preferred Mode for Carrying Out the Invention Below, the apparatus for separating and storing blood components of the present invention is described based on a first embodiment, which is a preferred embodiment, while making reference to the drawings. The apparatus 1 for separating and storing blood components of the first embodiment, as shown in FIG. 1 and FIG. 2, is provided with a blood storage part 2 for storing fluid containing at least blood-derived humoral components and platelets; a component storage part 3 for storing at least a part of the components of the fluid stored in the blood storage part; and a linking part 4 aseptically linking the blood storage part 2 and the component storage part 3.

The term "blood" used herein indicates whole blood including hemocytes (erythrocytes, leucocytes, platelets) and plasma (serum) as a liquid component, and a liquid containing at least one of these (for example, blood collected by apheresis). Furthermore, the term "serum" used herein means a pale yellow liquid obtained by allowing collected blood to stand, resulting in a reduction in fluidity, followed by separation from the red coagulated block (clot). The meaning of "serum" according to the present invention is different from common serums in terms of the production process not including separation from the clot, but it means a humoral component in the blood that is useful in cell culture and that includes coagulation factors and growth factors substantially equivalent to those in common serums.

The term "blood derived humoral component" used herein indicates "blood components other than hemocytes" or "mixture of blood components other than hemocytes and an agent such as an anticoagulant added thereto".

Figure 2:
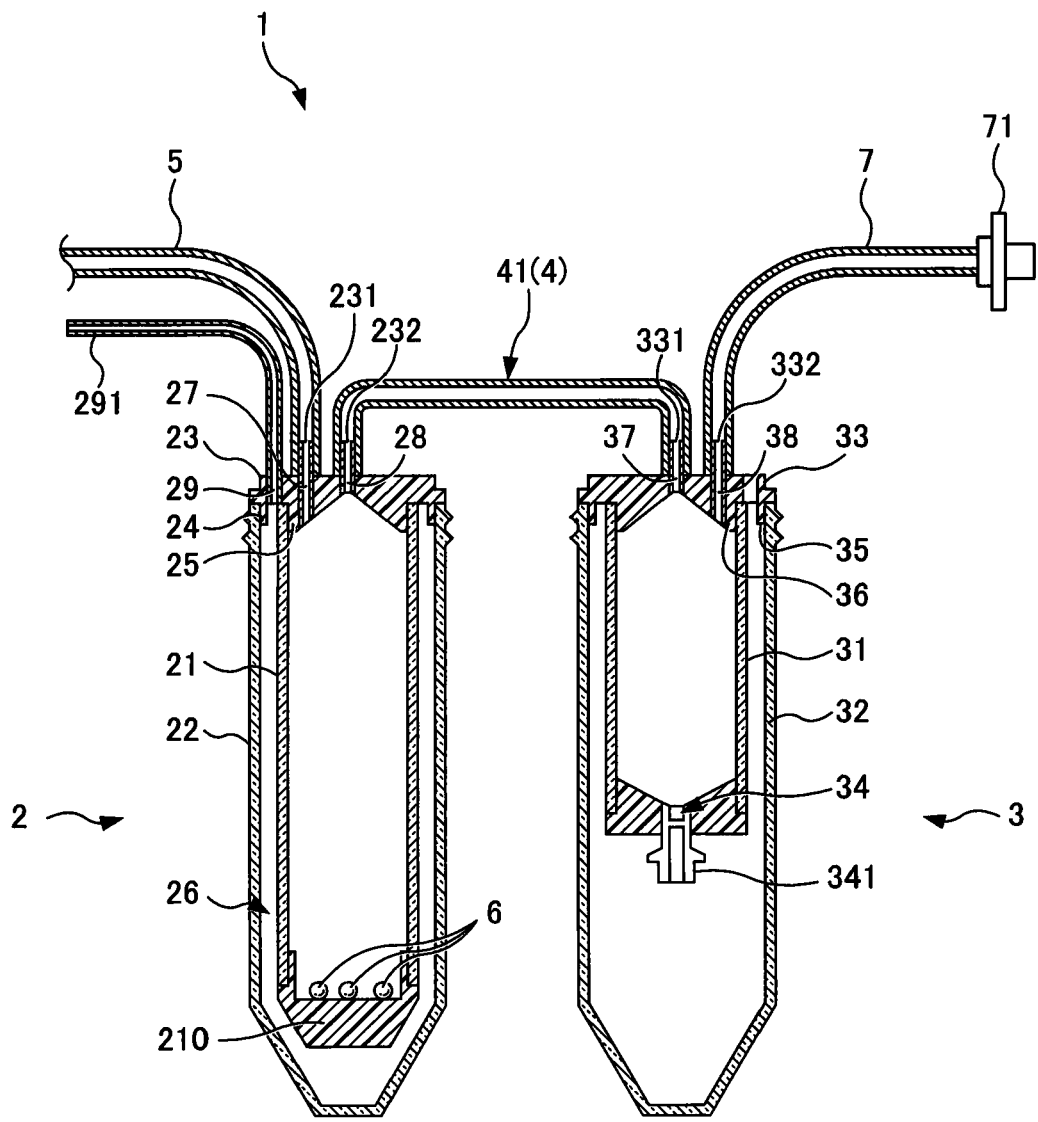
FIG. 2 is a partially expanded view of FIG. 1.

The blood storage part 2, as shown in FIG. 2, is provided with a blood storage container 21, a first storage container 22 for containing the blood storage container 21, and a first cap 23 connected to the blood storage container 21 and the first storage container 22.

The blood storage container 21, as shown in FIG. 2, has a longitudinal cylindrical shape, and is formed from a material whose side faces are flexible. Furthermore, a cross-section in a radial direction of the blood storage container 21 has an elliptical shape.

A side face of the blood storage container 21 is preferably composed of material that is transparent from a viewpoint in which fluid stored inside the blood storage container 21 is visible. For the flexible material it is possible to use polyvinyl chloride, polyethylene, polypropylene, polyurethane, silicone, ethylene-vinyl acetate copolymer resin, synthetic rubber, and soft synthetic resin such as various types of elastomer. An upper end which is one end of the blood storage container 21 has an opening, and is hermetically sealed by fitting the first cap 23. A bottom cap 210 is fitted to a lower end portion which is the other end of the blood storage container 21, and is joined by an adhesive.

The bottom cap 210 is provided with a cylindrical fitting part 211 and a bottom part 212 contiguous with this fitting part. A cross-section in a radial direction of the fitting part 211 has an elliptical shape, and an external diameter thereof is approximately the same as an internal diameter of the blood storage container 21. With regard to the bottom cap 210, the fitting part 211 fits a lower end part of the blood storage container 21. The diameter of the bottom part 212 gradually decreases in a downward direction, after which a bottom face thereof has a flat shape.

The first storage container 22, as shown in FIG. 2, has a cylindrical shape longitudinally similar to the blood storage container 21, and is configured such that its diameter and height are both larger than the blood storage container 21. An upper end which is one end of the first storage container 22 also has an opening, and can be hermetically sealed by fitting the first cap 23. In a vicinity of a lower end portion which is another end of the first storage container 22, the diameter of the first storage container 22 gradually decreases in a downward direction, after which it has an upper-lower reversed conical shape with a flat bottom face on the head thereof.

The first storage container 22 preferably is formed from material that is transparent from a viewpoint in which fluid stored inside the blood storage container 21 is visible, and is preferably formed from material having relatively large rigidity. With regard to the material of which the first storage container 22 is composed, specifically, polycarbonate, polyethylene, polypropylene, polyester, polymethylpentene, methacryl, ABS resin (acrylonitrile butadiene styrene copolymer), PET resin (polyethylene-telephthalate), and hard synthetic resin such as polyvinyl chloride may be cited. The hard synthetic resin refers to synthetic resin having hardness of an extent that does not easily deform due to a pressure variation of an internal space of a container due to injection of fluid to be described later.

A screw ridge is formed on an outer side face in a vicinity of the upper end of the first storage container 22, and a cover cap (not shown in the drawings) having a screw trough corresponding to the screw ridge can be screwed on. By screwing the cover cap onto the first storage container 22, it is possible to prevent the first cap 23 from coming off the first storage container 22 during a blood separation and storing operation, as described later.

The first cap 23 has a flat face with a circular shape, and its diameter is approximately the same as the outer diameter of the first storage container 22 (refer to FIG. 2). The first cap 23, on a lower face that is one face thereof, has a first connecting part 24 that can be connected to the first storage container 22, and a second connecting part 25 that can be connected to the blood storage container 21 on an inner side of the first connecting part 24. The first connecting part 24 and the second connecting part 25 have shapes that protrude in a downward direction.

An outer diameter of the first connecting part 24 is approximately the same as an inner diameter of the opening of the first storage container 22, and the opening vicinity of the first storage container 22 can be fitted to an outer peripheral face of the first connecting part 24. An outer diameter of the second connecting part 25 is approximately the same as an inner diameter of the opening of the blood storage container 21, the opening vicinity of the blood storage container 21 can be fitted to an outer peripheral face of the second connecting part 25.

That is, in the first embodiment, the blood storage container 21 and the first storage container 22 that contains the blood storage container 21 are both configured to be fitted to the first cap 23. The first storage container 22 is hermetically sealed by being fitted to the first cap 23. Furthermore, in this way, a pressure regulation space 26, which is a space independent of an inner space of the blood storage container 21, is formed between an outer side of the blood storage container 21 and an inner side of the first storage container 22.

A hermetically sealing member (not shown in the drawings) for improving sealing of the pressure regulation space 26 is interposed between the outer peripheral face of the first connecting part 24 and an inner peripheral face in the vicinity of the opening of the first storage container 22. In this way, it is possible to ensure a hermetically sealed structure with more certainty for the pressure regulation space 26.

As a hermetically sealing member, it is possible to use, for example, a ring shaped member formed from silicon rubber. The hermetically sealing member may have a configuration which can cap the outer peripheral face of the first connecting part 24; material is not limited to the abovementioned silicon rubber, and it is possible to used elastic members such as various types of rubber, various types of elastomer, and the like.

Furthermore, the hermetically sealing member may be disposed between an outer peripheral face of the second connecting part 25 and an inner peripheral face in the vicinity of the opening of the blood storage container 21.

The blood storage part 2 is provided with a fluid inlet channel 27 for introducing the fluid into the blood storage container 21, and a component outlet channel 28 for extracting at least a part of the components of the fluid from the blood storage container 21. In the first embodiment, the fluid inlet channel 27 and the component outlet channel 28 are arranged in the first cap 23, as shown in FIG. 2. The fluid inlet channel 27 and the component outlet channel 28 are arranged by forming a through hole penetrating the first cap 23 from an upper face thereof to a lower face.

The shape of a portion facing the inner space of the blood storage container 21, with regard to the lower face of the first cap 23, as shown in FIG. 2, is preferably formed to have a gradually decreasing diameter in an upward direction. In addition, a preferable configuration is one in which the component outlet channel 28, which is a through hole in a top part thereof, is provided. With the abovementioned configuration, when serum that is separated inside the blood storage container 21 is extracted to the component storage container 31, it is possible to draw out the serum without waste.

A blood drawing tube 5 is connected to the fluid inlet channel 27, and blood drawn from a subject passes through the blood drawing tube 5 and the fluid inlet channel 27, to be stored aseptically in the blood storage part 2 (the blood storage container 21). The fluid inlet channel 27 and the blood drawing tube 5 are connected by engaging an end part of the blood drawing tube 5 with a first protruding part 231 arranged on an upper face side in a portion in which the fluid inlet channel 27 is formed, in the first cap 23.

The blood storage container 21 contains a blood coagulation accelerating substance 6 that is in contact with the fluid and that accelerates coagulation of the fluid. The blood coagulation accelerating substance 6 is included to an extent such that blood coagulation factors such as fibrin, platelets, or the like can be activated, and preferably is insoluble in blood. By the blood coagulation accelerating substance 6 being insoluble in blood, it is possible to avoid a situation where impurities are mixed in the serum that is obtained.

Furthermore, in a case where the serum is prepared from blood, by activation of factors that are to be activated, such as platelets, blood coagulation factors and the like, centrifuge separation is performed, but from an aspect of suppressing destruction of red blood cells (hemolysis) and damage to the blood storage part, it is preferable that the exterior form of the blood coagulation accelerating substance 6 be approximately spherical. In addition, from a viewpoint of rapidly activating the abovementioned factors that are to be activated, a surface of the blood coagulation accelerating substance 6 is preferably formed with a layer formed from a compound of silicon dioxide.

At least one type selected from glass, silica, diatomaceous soil, kaolin, or the like can be used as the silicon dioxide compound, but there is no limitation to these. In the first embodiment, approximately spherical glass-formed objects are used as the blood coagulation accelerating substance 6.

Setting surface area of the blood coagulation accelerating substance 6 inside the blood storage container 21 to have a relationship of 0.1 to 25 $mm^2$/ml with the amount of blood that can be stored in the blood storage container 21 is preferable from aspects of both promotion of activation and suppression of hemolysis.

The blood storage part 2, as shown in FIG. 2, is provided with an injection hole 29 through which fluid can be injected into the pressure regulation space 26. Furthermore, an injection means (not shown in the drawings) that is linked to the injection hole 29 and injects fluid into the pressure regulation space 26 is provided at the injection hole 29. In the first embodiment, the injection hole 29 is arranged in the first cap 23. In detail, the injection hole 29 is a through-hole arranged in the first cap 23, and is formed in an area on an outer side of the second connecting part in the first cap 23 and an inner side of the first connecting part.

One end of a fluid injection tube 291 is connected to the injection hole 29, and an injection means is connected to the other end of the fluid injection tube 291. A pump, syringe, or the like can be used as the injection means.

By injecting fluid from the injection hole 29 by the injection means, the pressure regulation space 26 is pressurized. At this time, since the first storage container 22 forming an outer side of the pressure regulation space 26 is flexible, the blood storage container 21 is affected by the increased pressure of the pressure regulation space 26 and is deformed as if being crushed. Furthermore, the blood storage container 21 that is deformed as if being crushed by the pressurization of the pressure regulation space 26 is restored to its original shape by depressurizing the pressure regulation space 26 that has been pressurized. In this way, by deforming the blood storage container 21 by pressurizing and depressurizing the pressure regulation space 26, it is possible to easily and aseptically extract components of serum, to be described later, into the component storage part 3, and taking of blood.

The fluid that is injected into the pressure regulation space 26 may be a gas such as the air, or may be a liquid such as water. Furthermore, a gel form may be used as the fluid. In a case of using a fluid such as water or a substance in a gel form as the fluid, the volume of the fluid changes due to added pressure at time of injection, and this is preferable in that it is possible to accurately comprehend the amount of serum and the like that is extracted to the component storage part 3.

A linking part 4, as shown in FIG. 2, aseptically links the blood storage part 2 and the component storage part 3. In the first embodiment, the linking part 4 is formed from a linking tube 41, and links the component outlet channel 28 formed in the first cap 23, and the component inlet channel 37 formed in the second cap 33, to be described later. The linking tube 41 and the component outlet channel 28 are connected by engaging one end of the linking tube 41 to a second protruding part 232 provided on an upper face side of a portion in which the component outlet channel 28 is formed in the first cap 23.

The component storage part 3, as shown in FIG. 2, is provided with the component storage container 31, a second storage container 32 that contains the component storage container 31, and the second cap 33 that is joined to the component storage container 31 and the second storage container 32.

The component storage container 31 has a longitudinal cylindrical shape, and is formed from material having a flexible side face. A material similar to the abovementioned blood storage container 21 can be used as the flexible material. An upper end, which is one end of the component storage container 31 has an opening, and is hermetically sealed by being connected to the second cap 33. A component collection orifice 34 for collecting blood components contained in the component storage container 31 is formed at a lower end part, which is the other end of the component storage container 31. The component collection orifice 34 is formed by providing a thin area of a thin film form at a part of a bottom face of the component storage container 31. Furthermore, a hollow cylindrical part 341 that protrudes downwards from the bottom face of the component storage container 31 is formed in an area formed at the component collection orifice 34. The blood components contained inside the component storage container 31 can be collected by breaking and puncturing the component collection orifice 34 with a puncturing tool such as a syringe needle or the like. At this time, since the hollow cylindrical part 341 is formed in an area formed at the component collection orifice 34, it is possible to assuredly puncture the component collection orifice 34 with the puncturing tool.

As shown in FIG. 2, the shape of the bottom face of the component storage container 31 is preferably formed to have a gradually decreasing diameter in a downward direction. In addition, the component collection orifice 34 is preferably arranged at an apex thereof. With the abovementioned configuration, when serum is collected inside the component storage container 31, it is possible to collect the serum that is to be collected, without waste.

Furthermore, distance between the position of the component collection orifice 34 provided in the bottom part of the component storage container 31 and the position of an inner face bottom part of the second storage container 32 is preferably set to a distance whereby the puncturing tool can be contained. With the abovementioned configuration, it is possible to contain the puncturing tool within the second storage container 32 in a state puncturing the component collection orifice 34 of the component storage container 31. If the configuration has an open-close structure whereby appropriate communication with the puncturing tool is possible, collection and storage of the serum inside the component storage container 31 is possible in accordance with requirements.

The second storage container 32 has a longitudinal cylindrical shape, and is configured such that its diameter and height are both larger than the component storage container 31. An upper end which is one end of the second storage container 32 also has an opening, and can be hermetically sealed by fitting the second cap 33. In a vicinity of a lower end portion which is the other end of the second storage container 32, the diameter of the first storage container 22 gradually decreases in a downward direction, after which it has an upper-lower reversed conical shape with a flat bottom face on the head thereof.

In the first embodiment, the second storage container 32 is formed from material the same as the abovementioned first storage container 22, and the shape and size thereof are the same as the first storage container 22.

A screw ridge, similar to the first storage container 22, is formed on an outer side face in a vicinity of the upper end of the second storage container 32, and a cover cap (not shown in the drawings) having a screw trough corresponding to the screw ridge can be screwed on.

The second cap 33, similar to the first cap 23, has a flat face with a circular shape, and its diameter is approximately the same as the outer diameter of the second storage container 32. The second cap 33 on a lower face, which is one face thereof, has a third connecting part 35 that can be connected to the second storage container 32, and a fourth connecting part 36 that can be connected to the component storage container 31 on an inner side of the third connecting part 35. The third connecting part 35 and the fourth connecting part 36 have shapes that protrude in a downward direction.

An outer diameter of the third connecting part 35 is approximately the same as an inner diameter of the opening of the second storage container 32, and the opening vicinity of the second storage container 32 can be fitted to an outer peripheral face of the third connecting part 35. An outer diameter of the fourth connecting part 36 is approximately the same as an inner diameter of the opening of the component storage container 31, the opening vicinity of the component storage container 31 can be fitted to an outer peripheral face of the fourth connecting part 36.

As shown in FIG. 2, a through hole 29a is provided in the second cap 33, but this through hole 29a need not be provided.

That is, in the first embodiment, the component storage container 31 and the second storage container 32 that contains the component storage container 31 are both configured to be fitted to the second cap 33. The component storage container 31 is hermetically sealed by being fitted to the second cap 33, and the second storage container 32 is also hermetically sealed by being fitted to the second cap 33.

The component storage part 3 has a component inlet channel 37 for introducing at least a part of the components of the fluid that have been drawn from the blood storage container 21. In the first embodiment, as shown in FIG. 2, the component inlet channel 37 is arranged in the second cap 33. The component inlet channel 37 is provided by forming a through hole penetrating the second cap 33 from a top face thereof to a bottom face.

The linking tube 41 is connected to the component inlet channel 37, and serum drawn from the blood storage container 21 is stored aseptically within the component storage part 3 (the component storage container 31). The component inlet channel 37 and the linking tube 41 are connected by engaging an end part of the linking tube 41 with a third protruding part 331 arranged on an upper face side in a portion in which the fluid inlet channel 37 is formed, in the second cap 33.

A ventilation channel 38 for air circulation to and from the component storage container 31 is provided in the component storage part 3, and a ventilation tube 7 provided with a ventilation filter 71 is further linked to the ventilation channel 38. In the first embodiment, the ventilation channel 38 is provided in the second cap 33. In detail, the ventilation channel 38 is a through hole provided in the second cap 33, and is formed in an area on an inner side of the fourth connecting part 36 in the second cap 33.

One end of the ventilation tube 7 is connected to the ventilation channel 38, and the ventilation filter 71 is connected to the other end of the ventilation tube 7. The ventilation filter 71 is a filter having a property by which air is passed but fluid is not passed, and bacteria are also not passed. That is, the ventilation filter 71 can aseptically circulate air to and from the inside the component storage container 31, from the linked ventilation channel 38. The ventilation channel 38 and the ventilation tube 7 are connected by engaging an end part of the ventilation tube 7 to a fourth protruding part 332 provided on an upper face side of a portion in which the ventilation channel 38 is formed in the second cap 33.

In the apparatus for separating and storing blood components 1 of the first embodiment having the abovementioned configuration, the blood storage part 2 (the blood storage container 21), the linking part 4 (the linking tube 41), and the component storage part 3 (the component storage container 31) are aseptically linked, and internal spaces in each of the blood storage container 21, the linking tube 41, and the component storage container 31 are kept in an aseptic state. As a result, by circulating air aseptically to and from the ventilation channel 38, the apparatus for separating and storing blood components 1 of the first embodiment can regulate the internal spaces in each of the blood storage container 21, the linking tube 41, and the component storage container 31, to an arbitrary pressure while aseptically maintaining an aseptic state.

Next, a description will be given concerning a preferable size of each component member in the apparatus for separating and storing blood components 1 of the first embodiment.

A stored amount of blood in the blood storage container 21 is preferably from 5 to 200 ml, and more preferably 5 to 50 ml. The blood storage container 21 specifically has a preferable internal diameter of 10 to 30 mm, and a preferable height thereof is 50 to 150 mm.

The stored amount of blood components in the component storage container 31, from the viewpoint that fluid components separated from the blood stored in the blood storage container 21 are assuredly stored, is preferably 40 to 100% of the blood storage amount in the blood storage container 21.

If the first storage container 22 and the second storage container 32 are of sizes that can respectively contain the blood storage container 21 and the component storage container 31, there is no particular limitation on size, but diameters thereof are preferably 10 to 30 mm, and heights thereof are preferably 50 to 150 mm. Furthermore, well known centrifuge separating tubes are preferably used as the first storage container 22 and the second storage container 32. By using the well known centrifuge separating tubes as the first storage container 22 and the second storage container 32, in a centrifuge separation step in a blood component separation operation described below, it is possible to perform the separation operation simply by using a normal centrifuge separator in which the centrifuge separating tube can be used.

When well known centrifuge separating tubes are used as the first storage container 22 and the second storage container 32, the volume of the centrifuge separating tubes, from the viewpoint of raising general usability in the centrifuge separation process, is preferably 5 to 50 ml.

Next, using FIG. 3 to FIG. 8 a description is given concerning one preferred mode of a blood component separation storing operation using the apparatus for separating and storing blood components 1 of the first embodiment having the abovementioned configuration.

Figure 3:
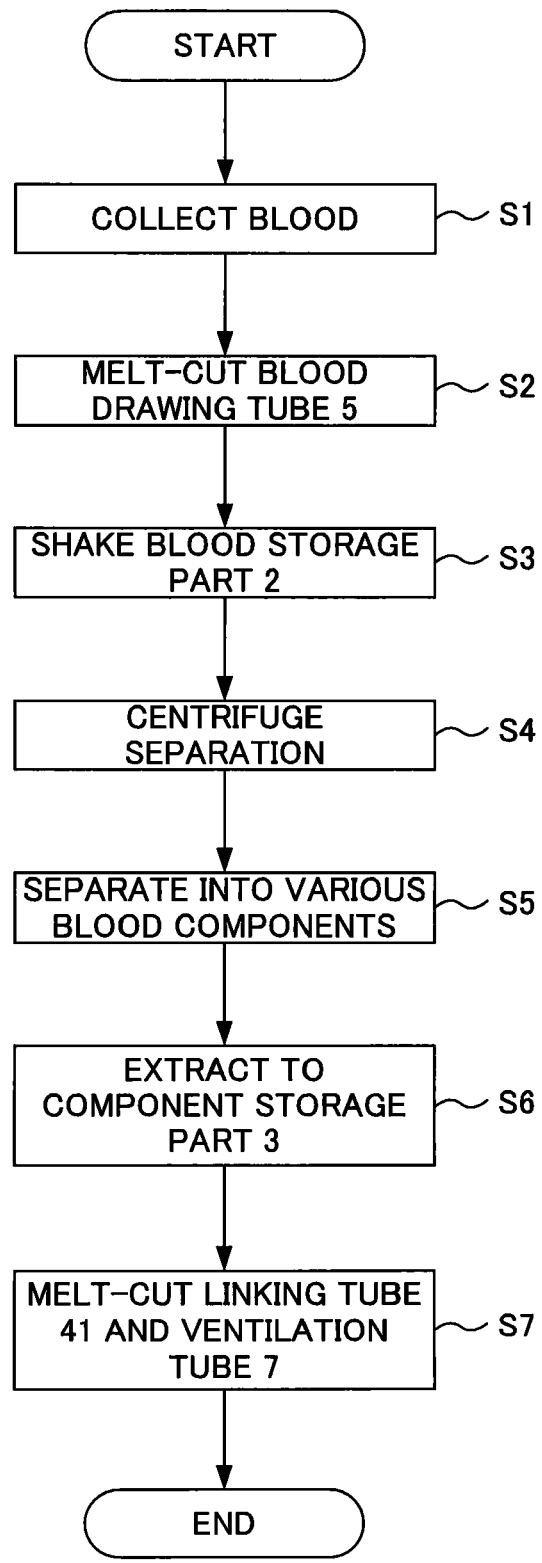
FIG. 3 is a drawing showing a procedure for performing separation and storing of blood components using the apparatus for separating and storing blood components of the first embodiment.
Figure 4:
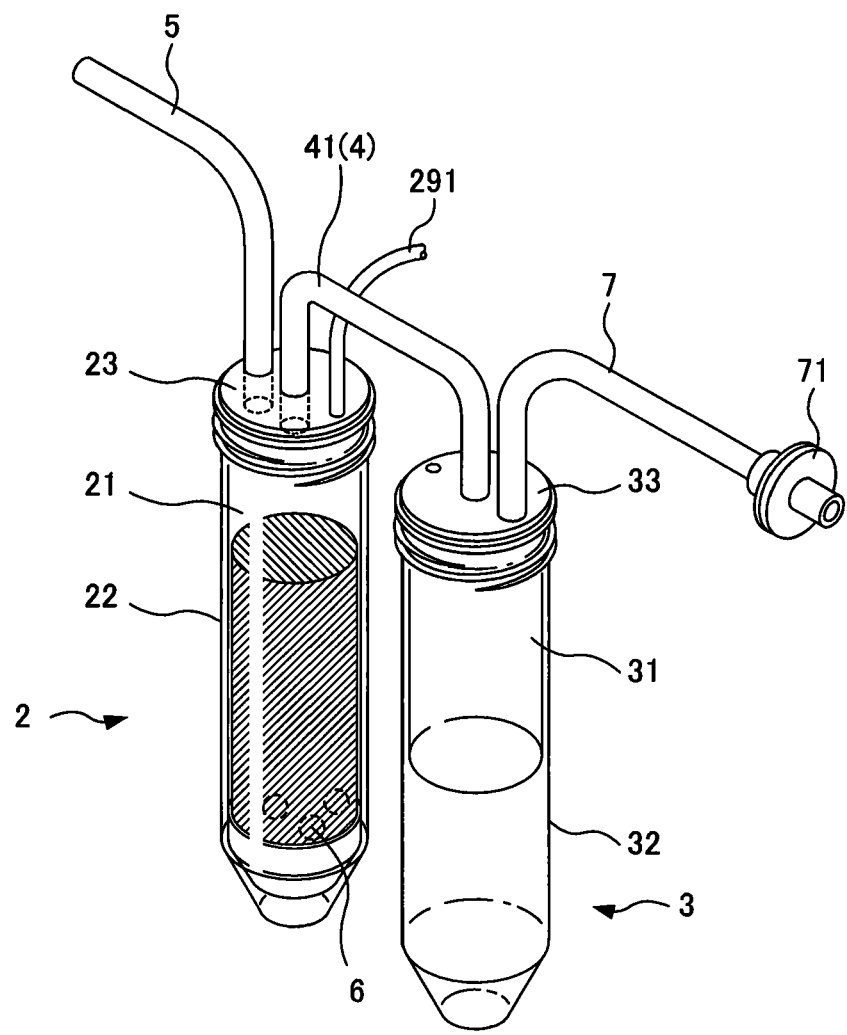
FIG. 4 is a drawing showing a storing process in an operation of separating and storing blood components using the apparatus for separating and storing blood components of the first embodiment.

As shown in FIG. 3, the blood component separation storing operation of the present mode is generally made up of 7 steps (S1 to S7).

First, in a storage step S1, as shown in FIG. 1, a blood drawing needle 80 is inserted into a subject (patient), and blood is drawn. At this time, the blood drawn by the blood drawing needle 80 is stored inside a blood storage part 2 (blood storage container 21), via a blood drawing tube 5 (refer to FIG. 4). When the blood is collected, by drawing in air from a ventilation filter 71 located at an extremity of a ventilation tube 7 provided in a component storage part 3, a negative pressure is applied inside a component storage container 31 and a blood storage container 21 communicating thereto, and it is possible to simply draw blood into the blood storage part 2. Furthermore, a non-return valve (not shown in the drawing) for preventing blood from back-flowing to the subject while blood is being drawn may be provided.

In addition, after the storage step S1, so that the blood collected in the blood storage part 2 does not flow towards the component storage part 3, a path of a linking tube 41 is closed at a source side of the blood storage part 2 by using a clamp (not shown in the drawings) or the like. In the storage step S1, consideration is given to the physical condition of a patient when blood is taken, a required amount is collected, and the step is completed. The required amount referred to here is approximately 5 to 50 ml when there is no problem with the patient's body size and condition.

After the storage step S1, the blood needle 80 is withdrawn from the subject of the blood collection, a part of the blood drawing tube 5, which connects the blood drawing needle 80 and the blood storage part 2, is melt-cut, and at the same time the melt-cut end is melted (melt-cut step S2). A melting cutter (not shown in the drawings) referred to as a sealer can be used in melt-cutting the drawing tube 5.

Figure 5:
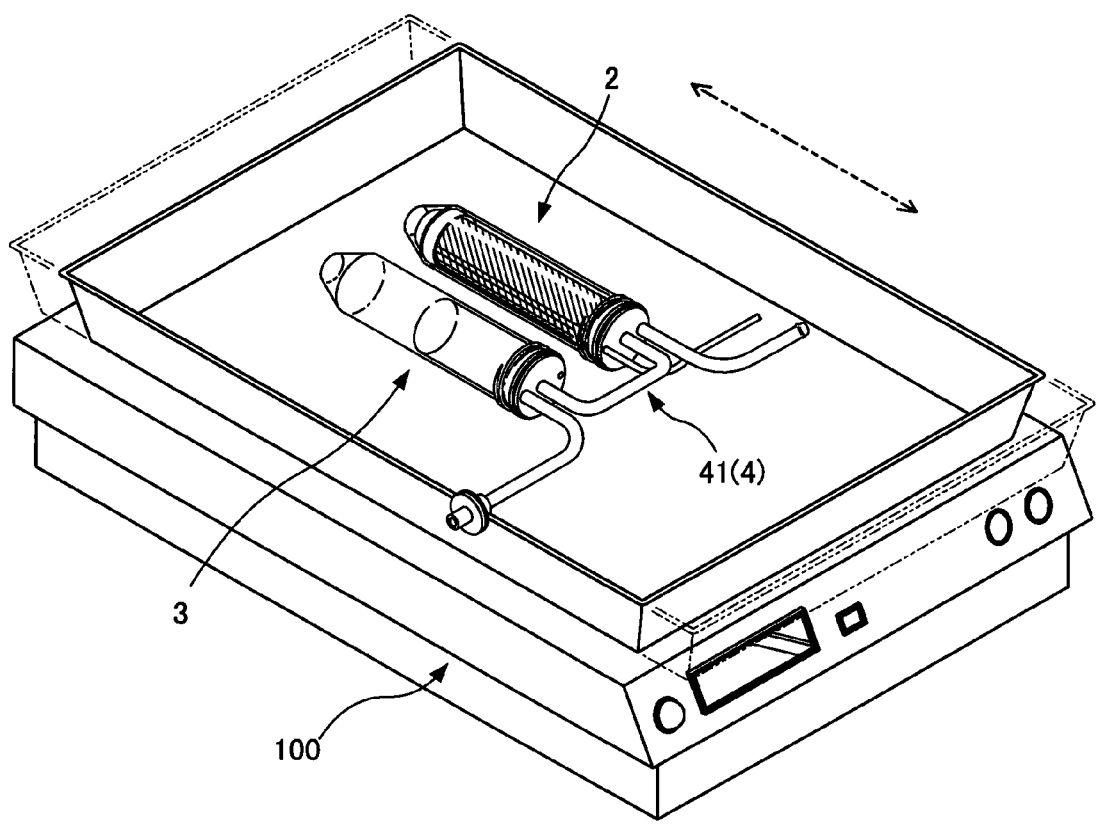
FIG. 5 is a drawing showing an activation promoting step in an operation of separating and storing blood components using the apparatus for separating and storing blood components of the first embodiment.

Next, as shown in FIG. 3 and FIG. 5, after completing the storage step S1, the blood storage part 2 is shaken (activation promotion step S3). In the activation promotion step S3, the blood storage part 2, which stores the blood that has been collected, is agitated gently by a shaking device 100, and contact is made with a blood coagulation accelerating substance 6 that is housed inside the blood storage container 21. Platelets and coagulation factors included in the blood are activated at the surface of the blood coagulation accelerating substance 6, and growth factors coming from the platelets that have been activated are emitted therefrom.

Figure 6:
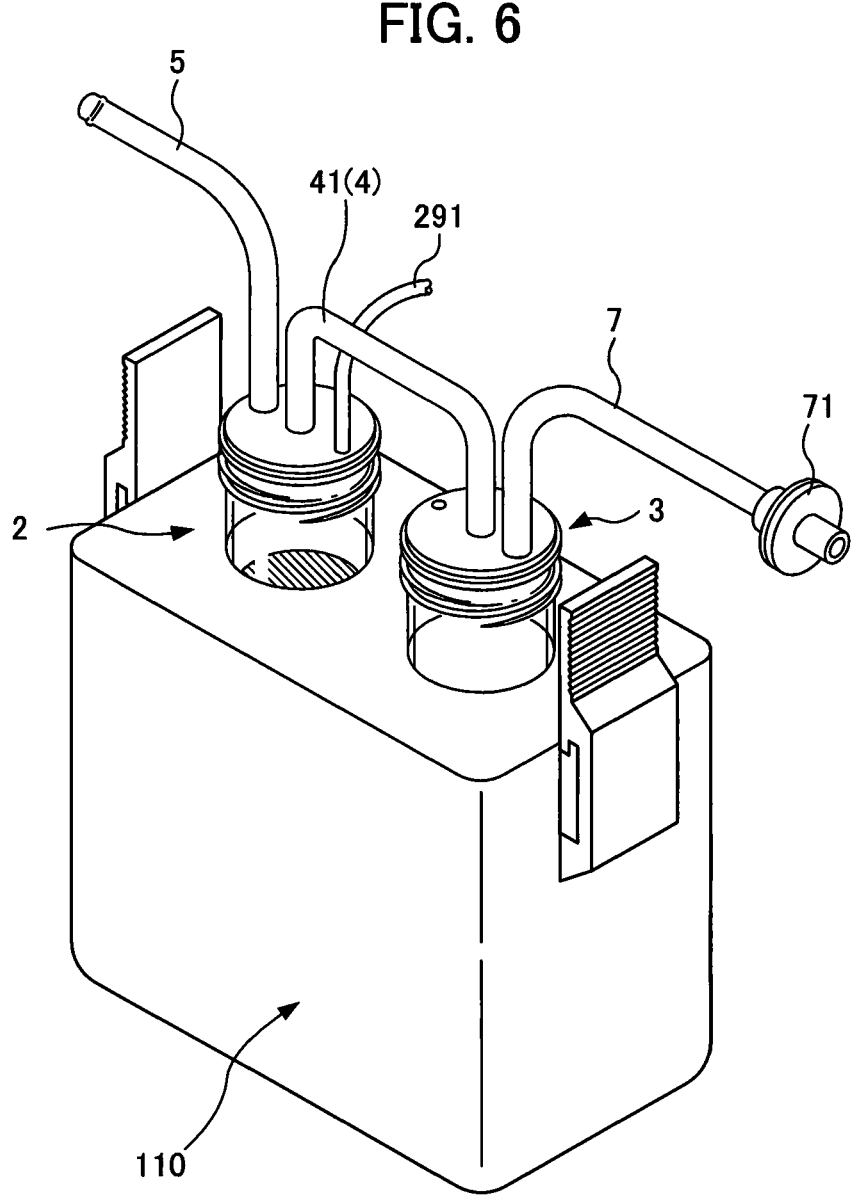
FIG. 6 is a drawing showing a state in which the apparatus for separating and storing blood components is contained in a centrifuge holder, in a centrifuge separation step in an operation of separating and storing blood components using the apparatus for separating and storing blood components of the first embodiment.

A centrifuge separator is applied to the blood storage part 2, which has been separated from the subject whose blood was collected after the activation promotion step S3 was done, together with the component storage part 3, the linking tube 41, the ventilation tube 7, and the like (centrifuge separation step S4). At this time, with the blood storage part 2 (the first storage container 22) and the component storage part 3 (the second storage container 32), in a case of using a well known centrifuge separation tube, as shown in FIG. 6, the blood storage part 2 and the component storage part 3 are inserted in a centrifuge holder 110 used for the centrifuge separator, and it is possible to perform centrifuge separation simply. The linking tube 41 is maintained in a state in which a path is closed by a clamp or the like (not shown in the figure) similar to the storage step S1.

A condition of the centrifuge separation with respect to the blood storage part 2 is that a setting is made according to the amount of blood stored and the type of components separated, and a setting is made, for example, to 2250 g×10 minutes at 4° C.

Figure 7:
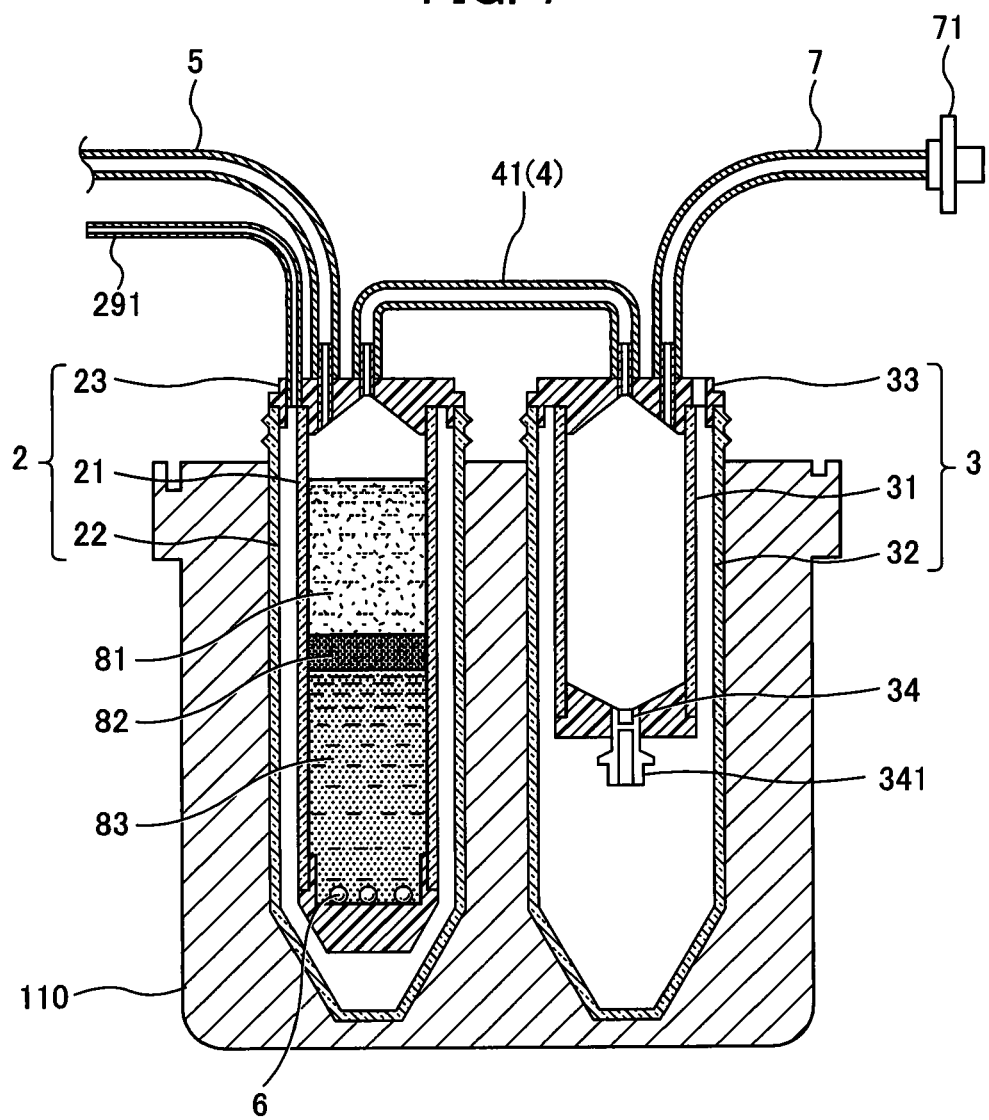
FIG. 7 is a drawing showing a state before which a pressure regulation space is pressurized, in a step of separating the blood components, in an operation of separating and storing blood components using the apparatus for separating and storing blood components of the first embodiment.

The blood that has undergone centrifuge separation after the activation promotion step S3 has been done, is generally separated and fractioned into 3 layers of serum 81, white blood cells 82, and red blood cells 83, inside the blood storage part 2 (the blood storage container 21), as shown in FIG. 7. Furthermore, the blood coagulation accelerating substance 6 sinks to the bottom of the blood storage container 21, in a state where coagulated bodies of the platelets and the coagulation factors are attached to the surface thereof.

The serum obtained after passing through the activation promotion step S3 and the centrifuge separation step S4, as described above, includes growth factors originating from the blood platelets and the coagulation factors adequately emitted in the activation promotion step S3.

The factors to be activated such as the platelets and the coagulation factors that have been activated in the activation promotion step S3 and the centrifuge separation step S4 attach to the surface of the blood coagulation accelerating substance 6, form aggregates, and are separated from the blood (separation step S5).

Figure 8:
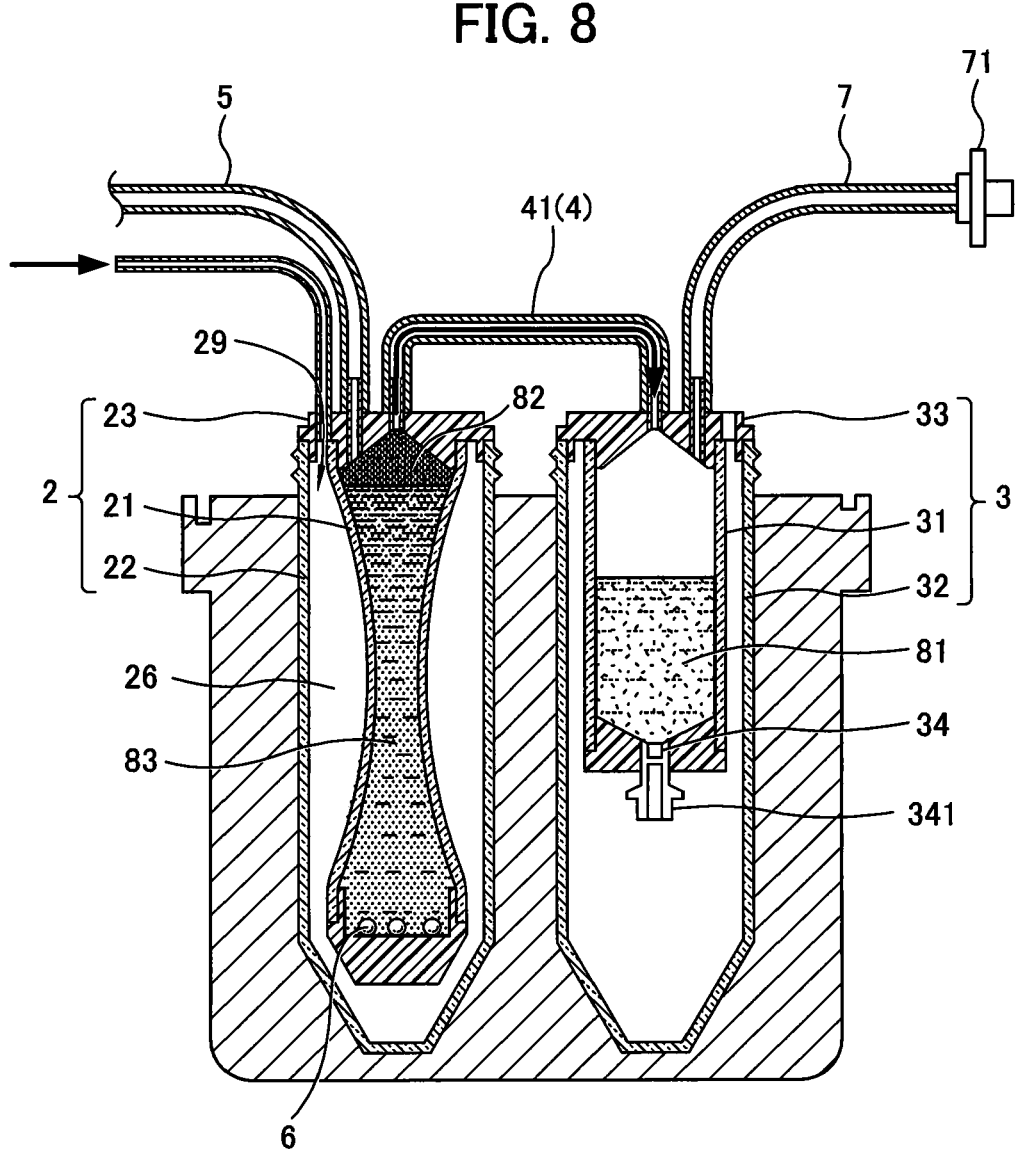
FIG. 8 is a drawing showing a state in which the pressure regulation space is pressurized, in a step of separating the blood components, in an operation of separating and storing blood components using the apparatus for separating and storing blood components of the first embodiment.

As shown in FIG. 8, in an extraction step S6, the serum 81 that was separated inside the blood storage container 21 in the separation step S5 is extracted to the component storage container 31 in the component storage part 3.

When the serum 81 separated inside the blood storage container 21 is extracted to the component storage container 31, as shown in FIG. 8, first the pressure regulation space 26 is pressurized by injecting fluid from the injection hole 29 to the pressure regulation space 26 formed between the blood storage container 21 and the first storage container 22 in the blood storage part 2. A pump, syringe, or the like can be used as the injection means for injecting the fluid, and a gas such as the air, a fluid such as water, or a substance in a gel form can be used as the fluid. Here, since the first storage container 22 forming an outer side of the pressure regulation space 26 is relatively rigid, the blood storage container 21, which has flexibility, is affected by increased pressure of the pressure regulation space 26 and deforms as if being crushed; the serum 81, which is supernatant that has been separated, is extracted via the linking tube 41 from the component outlet channel 28, and is drawn into the component storage part 3 (the component storage container 31).

In the extraction step S6, along with pressurization of the pressure regulation space 26 as described above, air may be drawn in from the ventilation filter 71 positioned at an extremity of the ventilation tube 7 provided in the component storage part 3. By drawing air from the ventilation filter 71, a negative pressure is applied inside the component storage container 31 and the linking tube 41 communicating therewith, and it is possible to draw the serum 81 from the blood storage container 21 to the component storage container 31 more easily.

After the component storage container 31 has been filled with the required amount of serum, the linking tube 41 and the ventilation tube 7 are melt-cut and melted (melt-cutting step S7). With regard to this melt-cut and melting, a method can be used that is the same as that of melt-cutting and melting the drawing tube before the centrifuge separation step S4. After the melt-cutting step S7, by performing what is referred to as an inactivation process (heating to 56° C. for 30 minutes) on the component storage container 31 that contains the serum, it is possible to inactivate complements within the serum. Furthermore, preservation treatment such as cryopreservation is applied to the component storage container part 3 which has been filled with serum inside the component storage container 31. Here, since the second storage container 32 containing the component storage container 31 is formed from a hard synthetic resin, when the contained serum is being transported and stored, it is possible to prevent the component storage container 31 from being damaged even if external force acts on the component storage part 3. Furthermore, when the component storage part 3 is stored, it is possible to easily attach a label or the like describing information concerning the contained contact.

According to the apparatus for separating and storing blood components 1 of the first embodiment having the abovementioned configuration, since the blood storage part 2 has the blood storage container 21 that has a cylindrical form and is flexible, it is possible to separate blood components more simply. Furthermore, since the blood storage part 2, the component storage part 3, and the linking part 4 that links these are connected aseptically, the blood or the serum is not affected by the external environment, the danger of the prepared serum being contaminated by microbes or the like is low, and it is possible to prepare the serum with a high degree of safety.

Furthermore, by the blood storage container 21 having a longitudinal cylindrical shape, even with a relatively small amount of blood collected, it is possible to easily separate the blood components, and it is possible to easily extract the separated components from the blood storage container 21. The ability to easily separate and store blood components even with a relatively small amount of blood in this way is particularly effective when preparing serum from the blood of a subject for which the amount of blood that can be drawn is limited. Here, a relatively small amount of blood indicates, in specific terms, a blood amount of approximately from 5 to 50 ml.

Furthermore, by forming the pressure regulation space between the blood storage container 21 and the first storage container 22 in the blood storage part 2 and the injection hole 29 for injecting the fluid into the pressure regulation space, it is possible to pressurize the pressure regulation space 26 and to deform the blood storage container 21 as if it were being crushed. In this way, by deforming the blood storage container 21 by pressurizing the pressure regulation space 26, it is possible to easily and aseptically draw the components of the serum and the like to the component storage part 3.

Furthermore, the blood storage container 21 that is deformed as if being crushed by pressurization of the pressure regulation space 26 is restored to its original shape by depressurizing the pressurized pressure regulation space 26. Therefore, before drawing blood the blood storage container 21 is deformed as if being crushed by pressurization of the pressure regulation space 26, and when blood is being drawn, the blood storage container 21 is restored to its original shape by depressurizing the pressure regulation space 26, and it is possible to easy draw blood with the inside of the blood storage container 21 having negative pressure.

In addition, a radial cross-section of the blood storage container 21 has an elliptical shape. In this way, the blood storage container 21 deforms easily in the short axial direction of the elliptical shape, and it is possible to easily draw the components of the serum and the like to the component storage part 3.

Furthermore, by the first storage container in the blood storage part 2 and the second storage container 32 in the component storage part 3 having a longitudinal cylindrical shape, postural maintenance of the apparatus for separating and storing blood components 1 that includes the blood storage part 2 and the component storage part 3 becomes easy, and operability of the blood component separation container is improved. Furthermore, with the first storage container 22 and the second storage container 32 having the same shape and having a prescribed shape, storage is possible in an ordinarily used centrifuge holder, without using a special support device, application is possible to the centrifuge separator, and the general applicability of the apparatus for separating and storing blood components 1 is improved. In addition, by containing the blood storage part 2 and the component storage part 3 in the centrifuge holder, since the disposition of the apparatus for separating and storing blood components 1 can be maintained, it is possible to use the centrifuge holder as an operational support device that can be commonly used in a series of steps extending from the blood storage step S1 to the melt-cutting step S7. The prescribed shape refers to cases of, for example, a shape similar to a 50 ml commercially available centrifuge settling tube.

Furthermore, since the blood coagulation accelerating substance 6 is contained in the blood storage container 21, blood clots adhere to the surface of the blood coagulation accelerating substance 6 when the serum is prepared, and mixing of blood clots and fibrin into the serum when the serum is separated is prevented.

Next, a description is given concerning a second embodiment of the apparatus for separating and storing blood components 1 of the present invention. In the second embodiment, the description will be mainly about points of difference from the above described first embodiment, and items are given the same reference symbols and descriptions thereof are omitted. For points that are not described in particular, descriptions concerning the first embodiment are applicable as appropriate.

The apparatus for separating and storing blood components 1 of the second embodiment differs from the first embodiment in that, in addition to an injection hole 29 provided in a blood storage part 2, a second injection hole 29a is provided in a component storage part 3.

Figure 9:
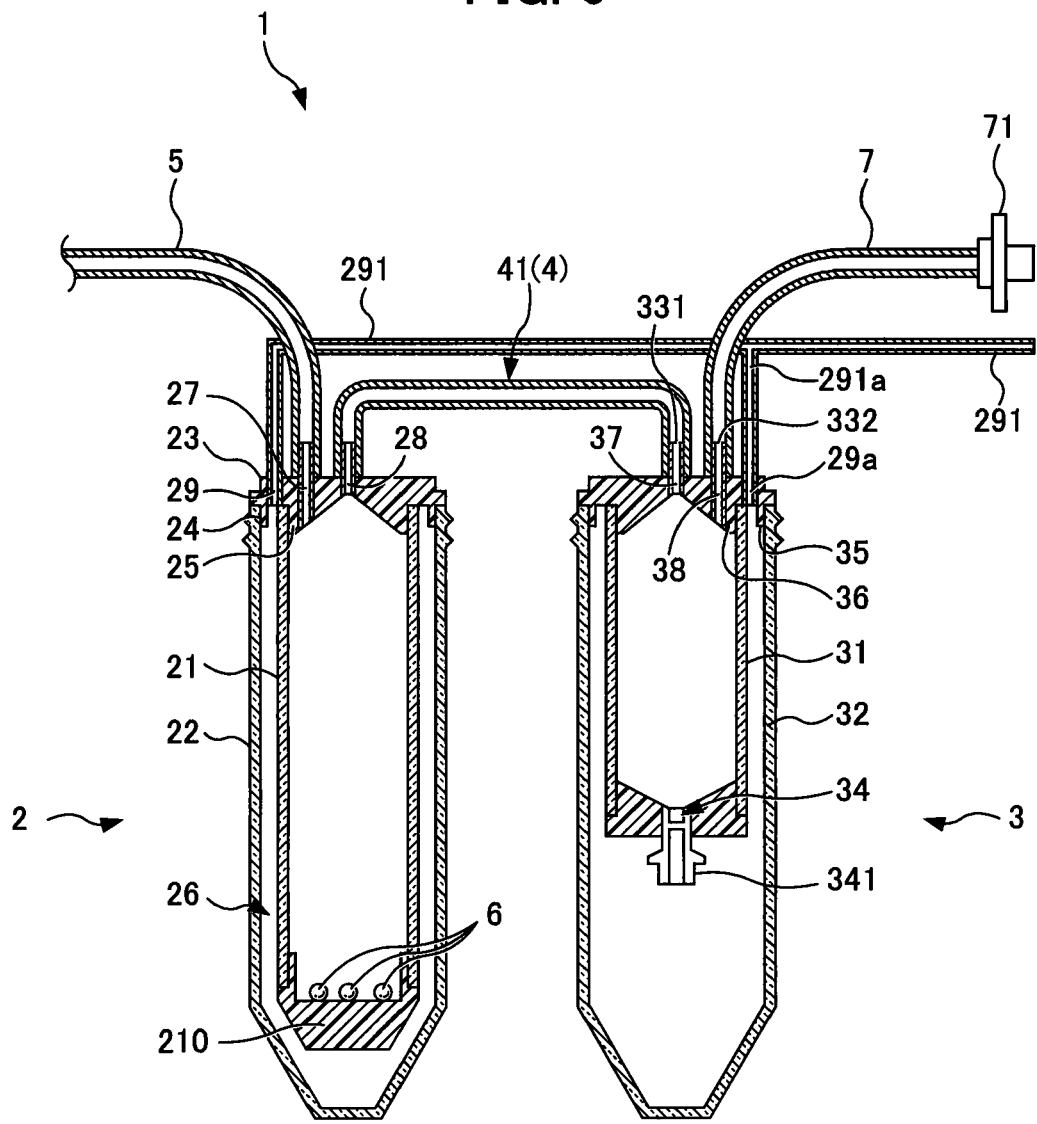
FIG. 9 is a partially expanded view showing a second embodiment of the apparatus for separating and storing blood components of the present invention.

In the apparatus for separating and storing blood components 1 of the second embodiment, the component storage part 3, as shown in FIG. 9, is provided with the second injection hole 29a that can inject fluid into a space provided between an outer face of a component storage container 31 and an inner face of a second storage container 32. In the second embodiment, the second injection hole 29a is provided in a second cap 33. In detail, the second injection hole 29a is a through hole provided in the second cap 33, and is formed on an outer side of a fourth connection part 36 in the second cap 33 and in a region of an inner side of a third connection part 35. One end of a second fluid injection tube 291a is connected to the second injection hole 29a. The other end of the second fluid injection tube 291a is linked to a prescribed position between two ends of a fluid injection tube 291, one end of which is connected to the injection hole 29 and the other end of which is connected to a fluid injection means (not shown in the drawings).

According to the apparatus for separating and storing blood components 1 of the second embodiment, by injecting fluid into a space formed between the outer face of the component storage container 31 and the inner face of the second storage container 32 in the component storage part 3, it is possible to regulate the pressure not only of a pressure regulation space 26 in the blood storage part 2, but also inside a space formed between the outer face of the component storage container 31 and the inner face of the second storage container 32. Therefore, for example, when blood is drawn in a blood storage step S1, when a negative pressure is applied inside the component storage container 31 and inside the blood storage container 21 communicating thereto by drawing air from a ventilation filter 71, by drawing fluid from the injection hole 29 and the second injection hole 29a by the fluid injection means together with drawing from the ventilation filter 71, it is possible to apply a negative pressure also to the space formed between the outer face of the component storage container 31 and the inner face of the second storage container 32, and to the pressure regulation space 26 in the blood storage part 2. In this way, by applying a negative pressure to both the space formed between the outer face of the component storage container 31 and the inner face of the second storage container 32, and to the pressure regulation space 26 together with drawing air from the ventilation filter 91, it is possible to prevent the component storage container 31 and the blood storage container 21 from being crushed due to drawing of air from the ventilation filter 71, and it is possible to prevent a decrease in an effect of drawing blood to the blood storage part 2.

The present invention has been described above based on preferred embodiments and modes, but the present invention is not limited to the abovementioned embodiments and modes and changes that do not depart from the scope of the invention are possible as appropriate.

For example, the connection between the first cap 23 and the blood storage container 21 or the first storage container 22, and the connection between the second cap 33 and the component storage container 31 or the second storage container 32 in the first embodiment and the second embodiment is by mating, but these connections may be, for example, by screwing together.

Furthermore, in the first embodiment and the second embodiment, a hermetically sealed member is interposed between the first cap 23 and the first storage container 22, but there is no limitation to this, and the hermetically sealed member may be interposed between the second cap 33 and the component storage container 31.

In addition, in the first embodiment and the second embodiment, the lower end part of the blood storage container 21 is formed from the bottom cap 210, but the lower end part of the blood storage container 21 may be formed by welding and sealing a flexible member forming a side face, at the lower end part.

Furthermore, the bottom cap 210 may be formed by a flexible member forming a side face.

In this way, by forming the bottom cap 210 by a member that has flexibility, the blood storage container 21 deforms easily in the bottom end part due to pressurization of the pressure regulation space 26, and it is possible to easily extract components such as serum or the like into the component storage part 3.

Furthermore, in the second embodiment, the fluid injection tube 291 and the second fluid injection tube 291a are linked together, but the two need not be linked. In addition, the fluid injection tube 291, the second fluid injection tube 291a, and the ventilation tube 7 may be linked.

Moreover, the blood coagulation accelerating substance 6 in the first embodiment and the second embodiment is a glass-formed object, but air may be used instead of the glass-formed object, or the glass-formed object and air may be used together.

Furthermore, transport of serum from the blood storage container 21 to the component storage container 31 in the first embodiment and the second embodiment is performed by deforming the blood storage container 21 by pressurizing the pressure regulation space, but the blood storage container 21 may be deformed by applying a negative pressure inside the component storage container 31 and the blood storage container 21 that communicates therewith, by drawing air from a ventilation channel.

In addition, the injection hole 29 in the first embodiment and the second embodiment is provided in the first cap 23, but may be provided on a side face of the first storage container 22.

Furthermore, the lower end parts of the blood storage container 21 and the component storage container 31 in the first embodiment and the second embodiment are configured to be at a distance from the respective inner sides of the first storage container 22 and the second storage container 32, but a configuration is also possible in which the two members are fixed by coming into contact or by means for mating together.

In addition, a configuration is possible in which a spacer (not shown in the drawings) is disposed between the lower end part of the blood storage container 21 and the bottom part of the first storage container 22, and between the lower end part of the component storage container 31 and the second storage container 32.

With the abovementioned configuration, in the centrifuge separation step in a blood component separation operation of the present apparatus, it is possible to reduce load placed on each of the blood storage container 21 and the component storage container 31.

Furthermore, the shape of a portion facing an internal space of the component storage container 31 at a lower face of the second cap 33, in the first embodiment and the second embodiment, as shown in FIG. 2 and FIG. 9, is configured with a form that gradually decreases in diameter in an upward direction, and the component inlet channel 37, which is a through hole, is arranged at an apex thereof.

Figure 10:
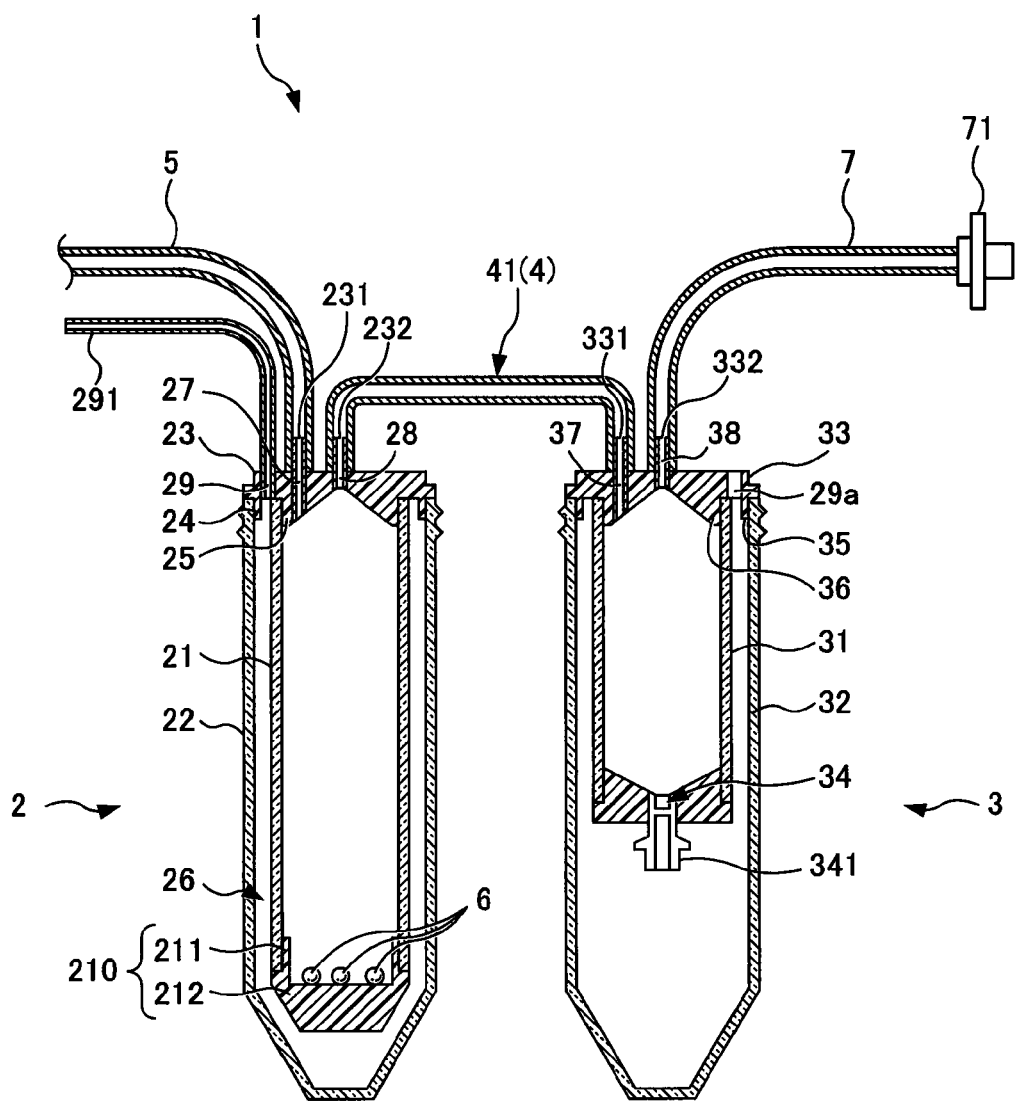
FIG. 10 is a view showing a modified example of the apparatus for separating and storing blood components of the first embodiment.

However, the present configuration may be configured such that the ventilation channel 38, which is a through hole, is arranged at an apex of the second cap 33 (refer to FIG. 10).

In this way, when air is drawn from the ventilation channel 38 to perform an operation of depressurizing inside the component storage container 31, it is possible to perform the operation of depressurization, without drawing components (for example, serum) contained inside the component storage container 31.

Furthermore, a blood cell removing filter (not shown in the drawings) may be interposed in an empty portion of any of the component outlet channel 28, the linking tube 41 or the component inlet channel 37. In this way, blood cell components in the blood storage container 21 can be captured by the blood cell removing filter, and it is possible to prevent mixing of the blood cell components into the component storage container 31.

The invention claimed is:

1. An apparatus for separating and storing blood components, the apparatus comprising: a blood storage part for storing fluid including at least a blood derived humoral component and platelets; a component storage part for storing at least a part of the components of the fluid stored in the blood storage part; and a linking part for aseptically linking the blood storage part and the component storage part; wherein the blood storage part has a blood storage container in the form of a flexible cylinder having an opening formed at one end, a first storage container having a cylindrical shape and an opening formed at one end, and containing the blood storage container, a first cap that fits the opening of the blood storage container and the opening of the first storage container, and said first cap hermetically seals the blood storage container and the first storage container, a fluid inlet channel that is provided in the first cap and is for introducing the fluid into the blood storage container, and a component outlet channel that is provided in the first cap and is for extracting at least a part of the components of the fluid from the blood storage container;

a pressure regulation space is formed in a space independent of an internal space of the blood storage container, between an outer side of the blood storage container and an inner side of the first storage container;

the component storage part has a component inlet channel for introducing at least a part of the components of the fluid that have been extracted from the blood storage container; and the linking part links the component outlet channel and the component inlet channel.

2. The apparatus for separating and storing blood components according to claim 1, wherein the blood storage part comprises an injection hole by which fluid can be injected into the pressure regulation space.

3. The apparatus for separating and storing blood components according to claim 2 further comprising an injection means, linked to the injection hole, for injecting fluid into the pressure regulation space, wherein the blood storage container deforms due to the fluid that is injected.

4. The apparatus for separating and storing blood components according to claim 2, wherein the injection hole is provided in the first cap.

5. The apparatus for separating and storing blood components according to claim 1, wherein the blood storage container contains a blood coagulation accelerating substance that comes into contact with the fluid and accelerates coagulation of the fluid.

6. The apparatus for separating and storing blood components according to claim 1, wherein the component storage part comprises: a component storage container of cylindrical shape, having flexibility, and having an opening at one end, a second storage container of cylindrical shape, having an opening at one end, and containing the component storage container, and a second cap connected to the opening in the component storage container and fitting the opening in the second storage container.

7. The apparatus for separating and storing blood components according to claim 6, wherein the component storage part has a ventilation channel in which circulation of air is performed with regard to the component storage container, wherein a ventilation tube provided with a ventilation filter is further linked to the ventilation channel.

8. The apparatus for separating and storing blood components according to claim 6, wherein the component storage container comprises a component collection orifice in a bottom part that is an end part different from one end at which the opening is provided in the component storage container.

9. The apparatus for separating and storing blood components according to claim 6, wherein the first storage container and the second storage container are approximately the same shape.

10. The apparatus for separating and storing blood components according to claim 1, wherein the blood storage part and the component storage part have a self-sustaining shape.

* * * * *